United States Patent
Muzzi et al.

(10) Patent No.: US 7,198,624 B2
(45) Date of Patent: Apr. 3, 2007

(54) APPARATUS WITH ULTRA VIOLET SPECTRUM LAMP, FOR THE TREATMENT OF PSORIASIS

(75) Inventors: Francesco Muzzi, Florence (IT); Alessandro Baldesi, Prato (IT)

(73) Assignee: EL.EN S.P.A. (IT)

( * ) Notice: Subject to any disclaimer, the term of this patent is extended or adjusted under 35 U.S.C. 154(b) by 165 days.

(21) Appl. No.: 10/489,982

(22) PCT Filed: May 2, 2002

(86) PCT No.: PCT/IT02/00287

§ 371 (c)(1), (2), (4) Date: Jul. 26, 2004

(87) PCT Pub. No.: WO03/024526

PCT Pub. Date: Mar. 27, 2003

(65) Prior Publication Data
US 2004/0249369 A1    Dec. 9, 2004

(30) Foreign Application Priority Data
Sep. 17, 2001   (IT) ............................ FI2001A0172

(51) Int. Cl.
*A61B 18/18* (2006.01)

(52) U.S. Cl. .................. 606/9; 606/3; 606/10; 606/12; 607/88

(58) Field of Classification Search .................... 606/3, 606/9–12; 607/88, 90, 91, 94; 128/898
See application file for complete search history.

(56) References Cited

U.S. PATENT DOCUMENTS

| | | | |
|---|---|---|---|
| 5,173,638 A | | 12/1992 | Eliasson et al. |
| 5,221,141 A | * | 6/1993 | Swanson ..................... 362/250 |
| 5,447,527 A | * | 9/1995 | Waldman ...................... 607/88 |
| 5,449,138 A | * | 9/1995 | Ciancio ................... 248/123.2 |
| 5,955,840 A | * | 9/1999 | Arnold et al. .............. 313/637 |
| 6,328,760 B1 | * | 12/2001 | James .......................... 607/88 |
| 6,413,268 B1 | * | 7/2002 | Hartman ....................... 607/94 |
| 6,436,127 B1 | * | 8/2002 | Anderson et al. ............. 607/89 |
| 6,979,327 B2 | * | 12/2005 | Spencer .......................... 606/9 |
| 2005/0143793 A1 | * | 6/2005 | Korman et al. ............... 607/94 |

FOREIGN PATENT DOCUMENTS

| | | |
|---|---|---|
| EP | 0 208 392 | 1/1987 |
| WO | WO 01/66186 | 9/2001 |

* cited by examiner

Primary Examiner—A. Farah
(74) Attorney, Agent, or Firm—McGlew & Tuttle, PC

(57) ABSTRACT

A phototherapy apparatus for the treatment of psoriasis which includes a dielectric-discharge excimer lamp 32, which is equipped with a reflector 34 and optical system 36 for ensuring a substantially uniform density of energy, is mounted on a maneuverable arm 40. The arm 40 is mounted to a stand 24. An electronic control unit 20 and a radiofrequency power supply unit 22 are connected to the lamp 32. A pipe of a cooling circuit 9 is connected to the lamp 32 via the arm 40. The pipe 9 connects to an air-liquid exchanger 3 with a de-ionizer having a temperature sensor 5 and a sensor 7. The sensors 5, 7 and 10 are connected to a microcontroller 12, which is connected to an operating panel 14 and to a display 16 and a printer 18. A hardware container 26 is provided on the stand to hold the radiofrequency power supply unit 22, the printer 28, the microcontroller 12, the control panel 30, and the air-liquid exchanger 3.

6 Claims, 2 Drawing Sheets

APPARATUS WITH ULTRA VIOLET SPECTRUM LAMP, FOR THE TREATMENT OF PSORIASIS

FIELD OF THE INVENTION

The present invention relates to a phototherapy apparatus intended for the treatment of psoriasis, which comprises a dielectric-discharge excimer lamp which emits incoherent light with a spectrum which has a well-defined peak in the wavelength range around 308 nm.

BACKGROUND OF THE INVENTION

Psoriasis is a non-contagious chronic skin disease, the cause of which is still unknown and which is typically characterized by thick red zones of the skin which are covered with silvery or whitish scales. The extent of the disease is variable, with small local areas or the whole of the surface of the body being affected. The disease may also affect the joints, nails and the mucous membranes.

Topical therapies are usually used for the less severe forms of psoriasis which are generally well defined and have the classic symptoms. Creams and ointments with a pharmacological action (keratolytic agents, tar, dithranol, cortisone preparations, calcipotriol, tacalcitol, tazarotene) or simply softening agents are used.

Systemic therapies are used for the more severe forms or the forms of common psoriasis which do not respond to topical treatment. These are more complete and effective therapies since they are applied to the whole of the organism. Precisely for this reason, however, they may also cause notable side effects: it is essential, therefore, that they should always be administered under the close supervision of a specialist doctor.

The most common systemic therapies use: methotrexate, cyclosporin A and retinoids. All these treatments give rise to significant side'effects and contraindications which are well known in literature and to specialists in the sector.

Phototherapy is also widely used.

Exposure to the sun has always been used for the treatment of psoriasis; it is therefore logical to imitate this using artificial sources so that it is readily available. Phototherapy is based on the application of ultraviolet radiation (UV). In the same way as visible light, which can be divided into the spectral colors ranging from violet to red, ultraviolet radiation can be divided into individual bands of varying wavelength. This division is performed on the basis of the biological effect caused and thus the following three bands are obtained:

UV-C 100–280 nm: sterilization
UV-B 280–315 nm: skin erythema
UV-A 315–380 nm: skin pigmentation The corneal layer absorbs most of the UV-B radiation which is then totally absorbed by the malpighian layer and by the dermis. The melanin absorbs, in addition to the heat, essentially the visible radiation; only a part of the UV-A radiation and the visible radiation reaches the dermis, while the red and infrared light passes through the epidermis and dermis and reaches the hypodermis.

There was a notable increase in the use of light sources for the treatment of psoriasis with the appearance of photochemotherapy (PUVA) which also awakened interest in other phototherapeutic methods. After a few years, however, the initial optimism regarding PUVA therapies was replaced by a certain skepticism; all the undesirable effects of the photosensitizing drugs became evident and the long-term side effects of the drugs used were not clear.

Over the years it was demonstrated that all the therapeutically effective radiant sources, including solar light (global radiation) use the range of 297 to 315 nm. In 1980 Parrish showed, in his experiments conducted on human beings, that the optimum efficiency in psoriasis treatment occurs in the range of 308 to 315 nm. This is the starting point of the principle of selective phototherapy, i.e. the use of a light source in which the spectral distribution of the energy contains a well-defined fraction of UV-B radiation (308–315 nm) necessary for obtaining the best therapeutic effect in the treatment of psoriasis.

At present two types of lamp are used: fluorescent lamps and metal—halogen lamps. The former have a wide active spectrum and must be used with filters which limit their spectrum, eliminating UVC and UVB radiation with a shorter wavelength; fluorescent tubes also have an emission with a wide spectrum and are limited to certain bands by specific coverings. Laser treatment of psoriasis has also been envisaged. This solution provides a very concentrated emission and therefore requires scanning along the surface to be treated. The use of laser and the implications of a concentrated emission mean that this solution is very costly and that particular care on the part of the operator is also required.

The solutions adopted hitherto also require the simultaneous use of drugs which may cause undesirable effects.

Moreover the use of coherent light, the wide nature of the range of radiation emitted and the use of corrective drugs are negative factors as regards specific treatment of the skin disorder in question.

SUMMARY OF THE INVENTION

The invention has been designed to optimize the therapy in question and simplify the operations involved therein. Thus an apparatus has been developed such as to allow the treatment, by means of radiation, of the patient's skin, in the zones to be treated, by means of a lamp which emits light with a spectrum which has a well-defined peak at the wavelength of 308 nm and which does not have undesirable effects.

The dielectric-discharge excimer lamp is preferably equipped with a reflector and optical system for ensuring a substantially uniform density of energy in the abovementioned range, at a distance of about 10–30 cm, on the skin of the patient to be treated.

Overall the apparatus comprises a stand and a hinged or maneuverable arm or any other projecting support for the lamp which can maintain the desired position and which extends from the stand so as to arrange the lamp in a suitable position with respect to the surface of the skin of the patient to be treated.

The apparatus is advantageously provided with a selective sensor for stabilizing temporally—i.e. in an instantaneous manner—the intensity of emission in the spectrum range concentrated around 308 nm.

The excimer lamp emits incoherent light, provides an emission of radiant energy which is not concentrated and able to allow the use of conventional optical reflective and refractive means; on the condition that there is control of the operating temperature—which can be easily achieved—this lamp concentrates the emission in the region of the desired value of 308 nm; moreover it does not require the simultaneous administration of drugs, thereby excluding undesirable effects. The form itself of the excimer lamp—extending in an elongated manner—allows easy treatment of surface zones, including large-size zones, with relative movements of lamp and patient which can be easily obtained without discomfort for the patient. In addition, the cost is much lower than that of the apparatus which has hitherto been suggested in literature and used.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 2:
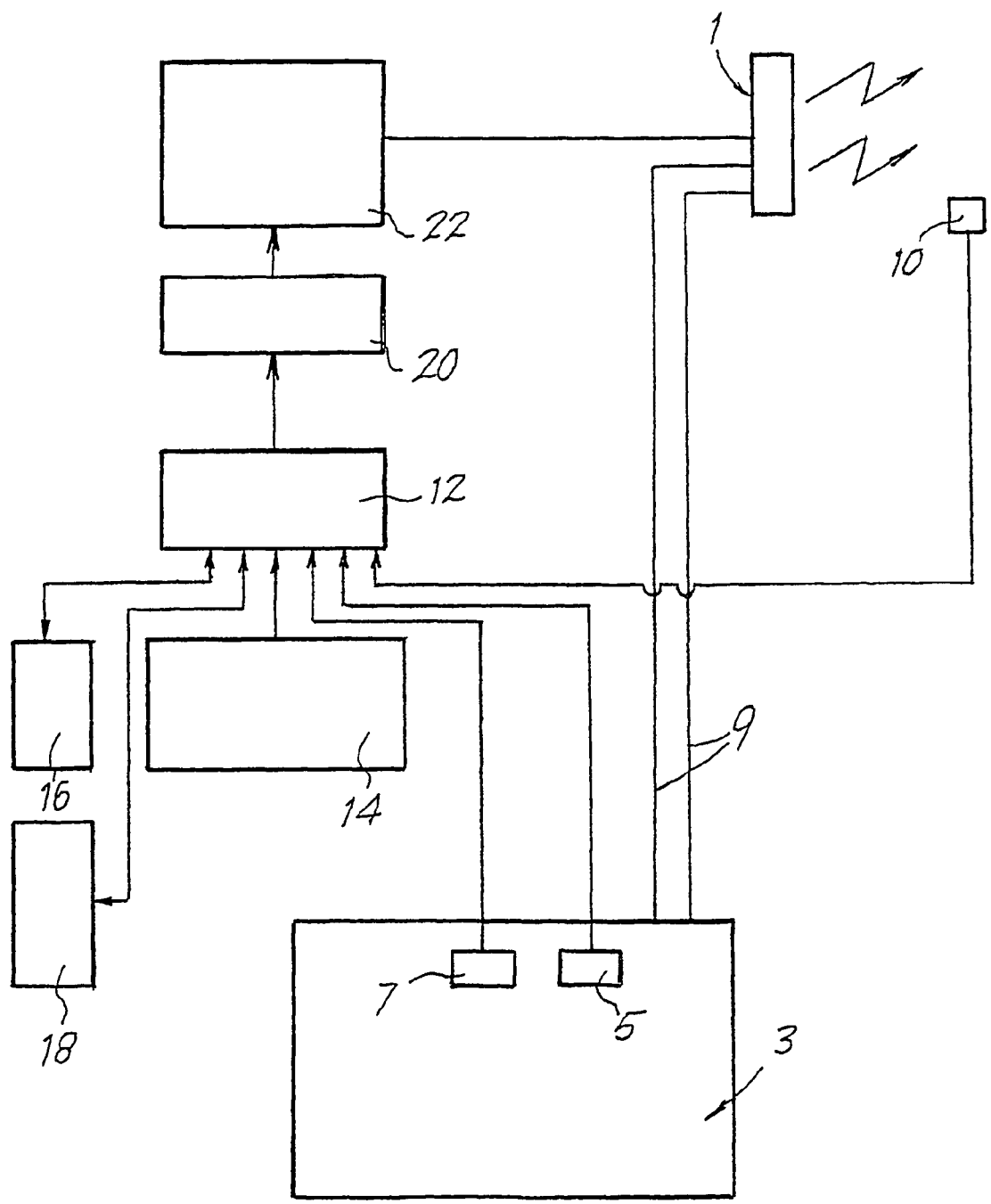
FIG. 2 shows a block diagram of said apparatus.

Referring to the drawings in particular, FIG. 2, 1 denotes the dielectric-discharge excimer lamp and associated accessories, in particular a reflector and an optical system for obtaining uniformity of the energy irradiated onto the skin of the patient; 3 denotes an air-liquid exchanger with a de-ionizer having, associated with it, a temperature sensor 5 and a sensor 7 for the flow of the cooling fluid, in order to avoid fluctuations in temperature. 9 denotes the liquid cooling circuit for the lamp; 10 represents a selective optical sensor. The sensors 5, 7 and 10 are connected to a microcontroller 12 connected to an operating panel 14, to a display 16 and to a printer 28. 20 represents an electronic control unit and 22 a radiofrequency power supply unit for the lamp 1.

Figure 1:
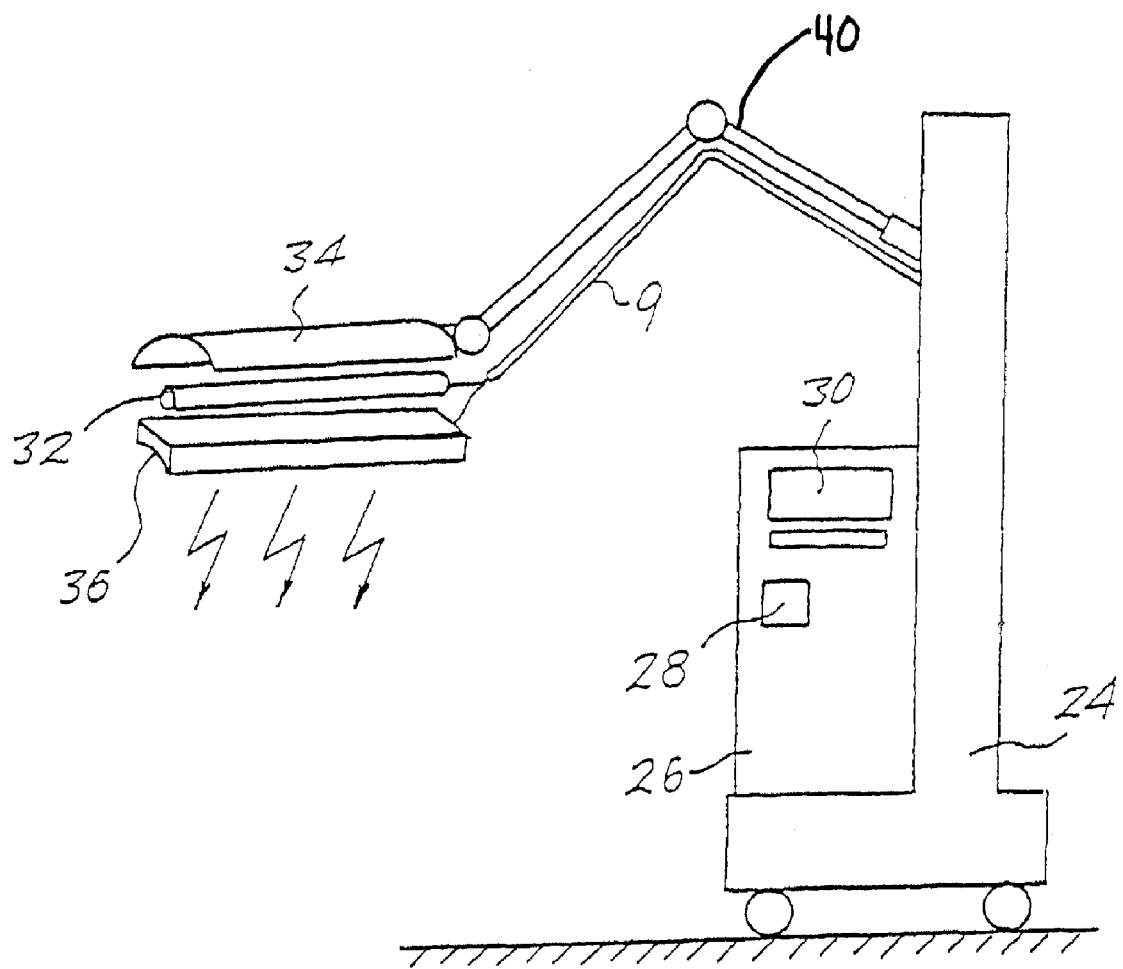
FIG. 1 shows schematically a possible structure of the apparatus for the treatment of psoriasis.

Structurally speaking, as shown in FIG. 1, 24 denotes a stand, 26 the hardware container for data processing, the management system, the radiofrequency power supply unit and the thermal conditioner. The container 26 also comprises the printer 28 and the control panel 30 for presentation of the data. An arm 40 which is hinged or in any case maneuverable and able to maintain the desired positions which are imparted to it in each case extends from the stand 24. The excimer lamp 32 with optical reflector 34 and with optical system 36 for obtaining the band of incoherent radiation used for the therapy is mounted on the end of said arm 40. The pipe 9 of the cooling circuit for the lamp, the cables for the lamp power supply and those for the sensors run along the said arm.

The apparatus uses the dielectric-discharge excimer lamp 32 provided with the reflector 34 and the optical system 36 which have the function of directing and ensuring uniform density of the energy which is emitted in the desired range and which must reach the skin of the patient to be treated from a distance of about 10–30 cm. The lamp is supported by the arm 40 which, in the equilibrium condition, may be positioned and fixed so as to remain in the desired position with respect to the patient, standing or seated or lying on the bed, if necessary in successive positions which are required for treatment of the various zones of the skin to be irradiated.

The RF power supply system and the electronic control unit which determines the emission at the desired wavelength and other components are driven by means of the microcontroller connected to the management panel which forms the interface with the operator. Control of the constancy of the level of intensity at the desired wavelength—in the region of 308 nm—is performed during feedback on the basis of the signal captured by the selective sensor centered on the desired wavelength. The intensity of the emission and the dose delivered are read from the display system of the machine/operator interface and recorded on a printer with which the apparatus is equipped, together with patient's data and other useful information.

The optical systems for homogenization of the beam are interchangeable with a group of systems of different construction so as to adapt the apparatus to the part of the patient to be treated.

The proposed system is suitable and may also be adapted for the treatment of textile products in order to obtain color toning and/or other—chemical-physical effects on fabrics or on yarns.

While specific embodiments of the invention have been shown and described in detail to illustrate the application of the principles of the invention, it will be understood that the invention may be embodied otherwise without departing from such principles.

The invention claimed is:

1. Phototherapy apparatus comprising:
    a dielectric-discharge excimer lamp, with a spectrum which has a well-defined peak in the range of wavelengths around the wavelength of 308 nm, said dielectric-discharge excimer lamp having a reflector and an optical system for making exiting light density substantially uniform;
    a stand;
    an arm, wherein said arm extends from said stand so as to arrange the lamp in a suitable position with respect to the surface of the skin of a patient to be treated;
    a selective sensor for sensing output of light intensity and maintaining emission output intensity in the spectrum range around 308 nm; and
    a sensor for detecting flow of a cooling liquid for cooling the lamp to prevent temperature fluctuations of the lamp.

2. Apparatus according to claim 1, wherein said reflector and said optical system ensure a substantially uniform density of energy in the desired band, at a distance of about 10–30 cm, on the skin of the patient to be treated.

3. A radiation generating apparatus comprising:
    a base unit;
    an optical system and a reflector for maintaining uniform density of energy irradiated to skin of a patient;
    a radiation source emitting radiation with a spectrum having a well-defined peak at the wavelength of 308 nm, said radiation source being located between said optical system and said reflector;
    a movable arm extending from said base unit to support said radiation source;
    means for cooling said radiation source;
    a selective sensor for sensing light intensity output and controlling the emission intensity output in the spectrum range around 308 nm; and
    a sensor for sensing flow of said means for cooling said radiation source.

4. Apparatus according to claim 3, wherein said reflector and optical system ensure a substantially uniform density of energy in the desired band, at a distance of about 10–30 cm, on the skin of the patient to be treated.

5. A radiation generating apparatus comprising:
    a base unit;
    a radiation source, adapted to emit radiation with a spectrum having a well-defined peak at the wavelength of 308 nm;

a reflector and radiation delivery optics coupled to said radiation source to maintain uniform density of energy irradiated to skin of a patient;

a movable arm extending from said base unit to support said radiation source;

a selective sensor for stabilizing emission intensity in the spectrum range around 308 nm, said selective sensor stabilizing emission intensity output during use of said radiation source; and a sensor for detecting flow of a cooling liquid for cooling said radiation source to prevent temperature fluctuations of said radiation source.

6. Apparatus according to claim 5, wherein said reflector and optical system ensure a substantially uniform density of energy in the desired band, at a distance of about 10–30 cm, on the skin of the patient to be treated.

* * * * *